United States Patent [19]

Tari

[11] Patent Number: 4,662,366

[45] Date of Patent: May 5, 1987

[54] IMMOBILIZING ARM SUPPORT

[76] Inventor: Lynda G. Tari, 3771 Elston Dr., San Bruno, Calif. 94066

[21] Appl. No.: 735,631

[22] Filed: May 20, 1985

[51] Int. Cl.⁴ .............................................. A61F 5/37
[52] U.S. Cl. ....................:............................ 128/134; 269/328
[58] Field of Search ................. 128/94, 133, 134, 135, 128/165; 269/322, 328; 378/208, 209; D24/49, 64

[56] References Cited

U.S. PATENT DOCUMENTS

| | | | |
|---|---|---|---|
| 2,306,715 | 12/1942 | Rubinstein | 128/94 |
| 3,554,194 | 1/1971 | Johnson | 128/94 |
| 3,861,666 | 1/1975 | Nishiyama et al. | 128/134 X |
| 3,888,244 | 6/1975 | Lebold | 128/165 X |
| 4,045,678 | 8/1977 | Rickard | 378/208 X |
| 4,265,232 | 5/1981 | Stonich | 269/328 X |
| 4,515,155 | 5/1985 | Wagemann | 128/134 |
| 4,531,942 | 7/1985 | Turner | 128/133 X |

Primary Examiner—Richard T. Stouffer
Attorney, Agent, or Firm—Robert Charles Hill

[57] ABSTRACT

An immobilizing arm support is disclosed for locating a patient's arm to facilitate angulated radiographic imaging, the arm support including a flexible sheet adapted for being wrapped about the patient 3 s upper and lower arm and held in place by straps, an immobilizing strap being attached to the sheet for engagement with a table supporting the patient, an extension of the sheet being wrapped about the patient's wrist or hand for supporting and preventing rotation of the lower arm. The arm support is substantially radioluscent and preferably is formed with a pocket in the sheet for receiving a rigidifying panel to minimize flexure of the patient's arm. The immobilizing strap is preferably formed as a separate element for selective attachment and detachment with the sheet.

18 Claims, 4 Drawing Figures

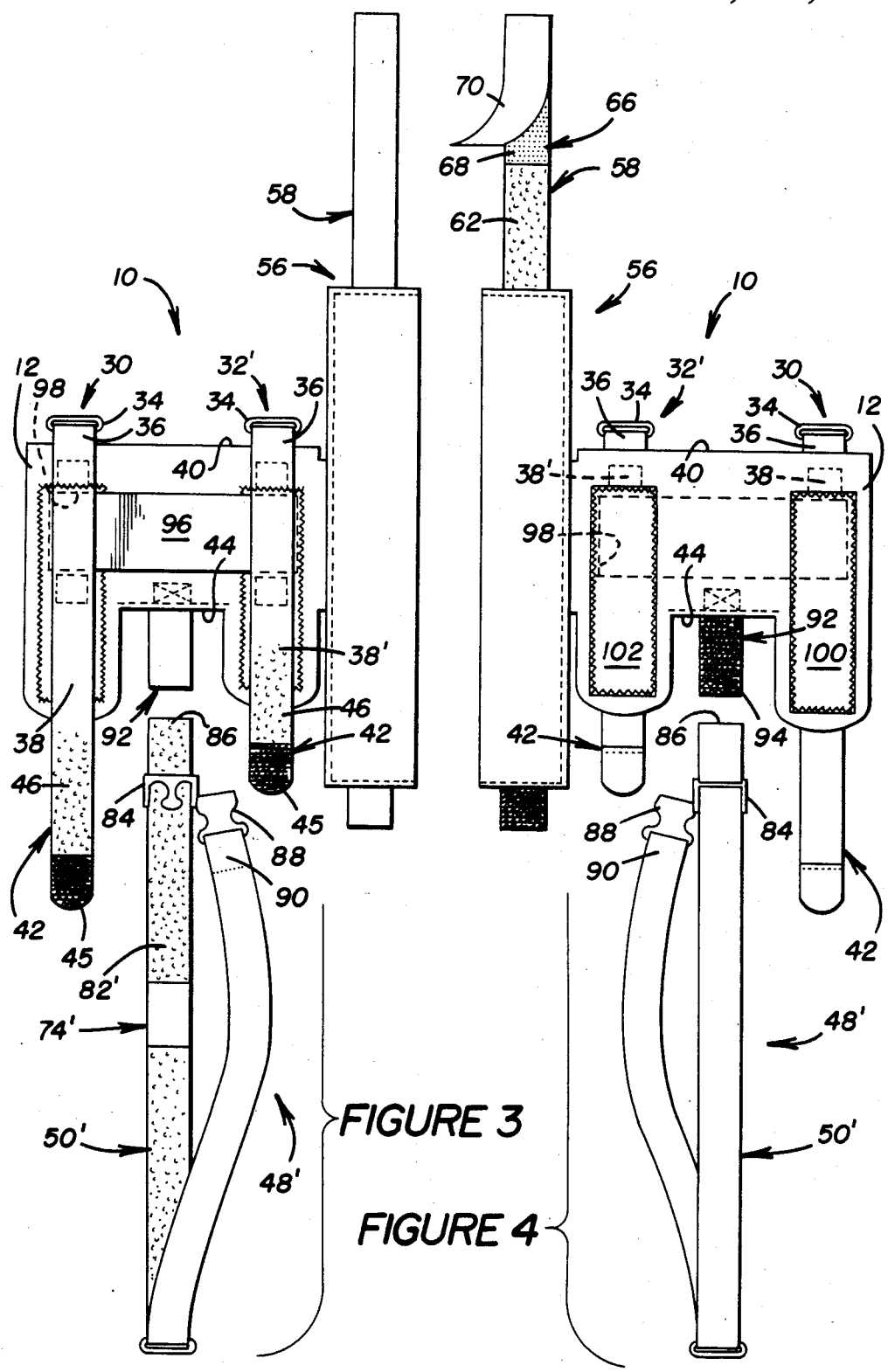

IMMOBILIZING ARM SUPPORT

The present invention relates to an immobilizing arm support for use in medical procedures and more particularly to an immobilizing arm support for locating a patient's arm to facilitate imaging of the patient by radiographic or other means during angioplasty procedures and the like with the patient being supine on a supporting table.

BACKGROUND OF THE INVENTION

In certain medical procedures, a patient is located in a supine position on a table or the like with one of a variety of imaging or radiographic techniques being used to provide an instantaneous or continuing representation of the patient's condition or response to the procedure. Often such procedures are directed toward the patient's coronary system and require accurate imaging of the chest cavity, particularly around the heart.

Furthermore, in order to obtain an accurate or more complete representation of the patient's condition, it is necessary to carry out the imaging techniques along a variety of axes in order to provide a more accurate or complete representation of a three-dimensional nature.

In particular, the present invention contemplates medical procedures having the object of reducing or eliminating blockage in the coronary system, especially adjacent the heart. The earliest of these procedures, and that used most commonly in the past, was the coronary bypass involving the use of surgical techniques for treating or removing the cause of blockage.

More recently, relatively non-surgical techniques have been developed for this purpose and are commonly used instead of coronary bypass surgery where possible. One such technique involves angioplasty procedures wherein a balloon catheter is introduced into the coronary arteries. This procedure is particularly effective for treating coronary blockage caused by localized deposits of plaque on the walls of the coronary vessels. The balloon catheter is caused to move through the coronary vessel until it is aligned within the constriction caused by the plaque. The balloon catheter is then expanded to form an enlarged passage through the vessel by causing the plaque to be adhered to the vessel wall.

Numerous variations of such angioplasty techniques are well known to those skilled in the art and do not require further discussion to permit a complete understanding of the present invention. However, it is noted that angioplasty, including newly developed laser angioplasty, may be either brachial or femoral in nature. That is, the catheter is introduced into the coronary system through an incision in the arm in brachial angioplasty or in the leg in femoral angioplasty.

In all such angioplasty techniques as well as in bypass surgery itself, very accurate radiographic imaging is necessary in order to properly observe the lesion or blockage in the coronary system and the effect of the treatment. Such an image or angiogram is obtained as a precursor to bypass surgery for diagnostic purposes. Similarly, angiographic procedures may be employed before, during and after angioplasty procedures to diagnose the initial condition of the patient and to monitor the effect of the procedure on the patient. Normally, the patient is arranged in a supine position on a supporting table or the like, imaging being carried out by a C-arm adapted to rotate about the patient so that the coronary system may be viewed from all angles.

Because of the relatively massive size of such imaging equipment, the area in which the patient is located within the rotating C-arm is quite limited. Furthermore, provision is normally made for immobilizing the patient's right arm during imaging, both to prevent the arm from interfering with the obtaining of clear images of the coronary system and also to maintain the patient in a fixed position while a number of images are obtained. In the past, the patient's right arm was arranged on rigid arm boards extending laterally from the side of the table supporting the patient.

With the patient in this position, it has been relatively easy in the past to obtain anterior-posterior or vertical views of the coronary system and even slightly angulated views with the C-arm rotated to permit imaging along a plane inclined from vertical. However, fully angulated or lateral imaging has presented difficulties for a number of reasons. Initially the laterally extending arm boards often physically interfere with the C-arm because of the relatively limited space provided for the patient and supporting table. Furthermore, with the arm boards extending laterally from the table, the patient's right arm tends to be positioned in or near the plane of the patient's heart which, as noted above, is the area of prime interest in such angiographic techniques.

Thus, both the patient's arm and the arm board tend to detract from fully angulated or lateral images since they are at least somewhat radiopaque and tend to cast shadows in the angiograms.

This difficulty in obtaining angulated angiograms naturally tends to interfere with the proper diagnosis and treatment of the patient by angioplasty techniques as well as with bypass surgery and the like where accurate and multiangled images are required.

Accordingly, there has been found a need for improved apparatus for facilitating angulated imaging of the coronary system of supine patients arranged on a supporting table or the like. In perfecting the present invention, it was initially discovered that prior restraints such as arm boards used in these procedures were undesirable for at least two reasons. Initially, the arm boards extended laterally from the table supporting the patient so that the arm boards as well as the patient's arm located on the arm boards tended to physically interfere with necessary rotation or positioning of the imaging equipment. Furthermore, both the patient's arms and the arm boards often prevented the obtaining of precise angulated images because of their relatively radiopaque nature and the position of the patient's arm generally in the plane of the heart.

SUMMARY OF THE INVENTION

It is therefore an object of the present invention to provide an immobilizing arm support for locating a patient's arm and facilitating angulated radiographic imaging during angioplasty procedures and the like, with the patient being on a supporting table or the like, while avoiding or overcoming one or more of the problems outlined above.

More particularly, it is an object of the invention to provide such an immobilizing arm support comprising sheet means adapted for wrapping about the patient's arm, upper and lower strap means for securing the sheet in wrapped relation about the patient's upper and lower arms, and an immobilizing strap for locating the patient's lower arm generally below the plane of the patient's heart. The arm support is substantially formed from radioluscent material.

It is an even further object of the invention to provide such an immobilizing arm support formed with two-piece construction in order to further facilitate positioning of the patient's arm in procedures of the type summarized above. Preferably, the immobilizing strap is adapted to pass about a bed or other support surface for the patient, the immobilizing strap being readily attachable and detachable from the remaining portion of the arm support.

It is yet a further related object of the invention to provide such an immobilizing arm support including an extension for the sheet means, the extension preferably being of a sufficient length to permit its being wrapped about the patient's lower arm adjacent the hand and attached to an adjacent element in order to support and minimize rotation of the patient's arm. Even more preferably, the extension includes a pad adapted for attachment to the adjacent element, the pad and another portion of the extension comprising adjustable mating fastener means to further facilitate positioning of the patient's arm.

Further objects and advantages of the invention are made apparent in the following description, having reference to the accompanying drawings.

BRIEF DESCRIPTION OF THE DRAWINGS

FIG. 1 may be seen as providing an oblique or offset, partially angulated view of the patient and arm support of the invention.

FIGS. 3 and 4 are plan views of opposite surfaces of an arm support constructed according to the present invention, the arm support of FIGS. 3 and 4 being arranged in a flat condition prior to being wrapped about the patient's arm. The arm support of FIGS. 3 and 4 illustrates a variation of the invention with respect to the arm support construction illustrated in FIGS. 1 and 2.

DESCRIPTION OF THE PREFERRED EMBODIMENT

Figure 1:
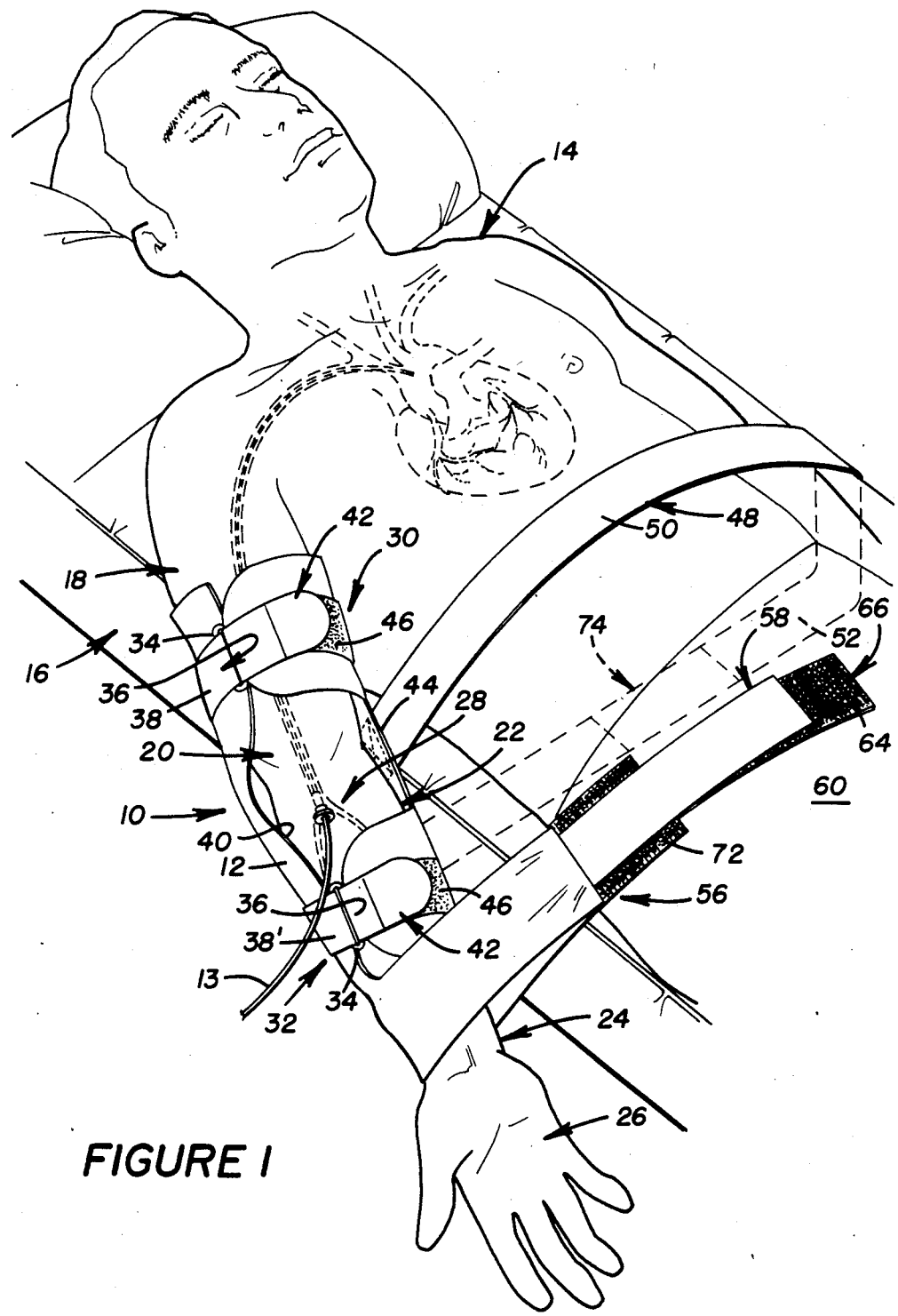
FIG. 1 is a perspective view of a patient located on a table with an immobilizing arm support constructed according to the present invention serving to position the patient's arm.
Figure 2:
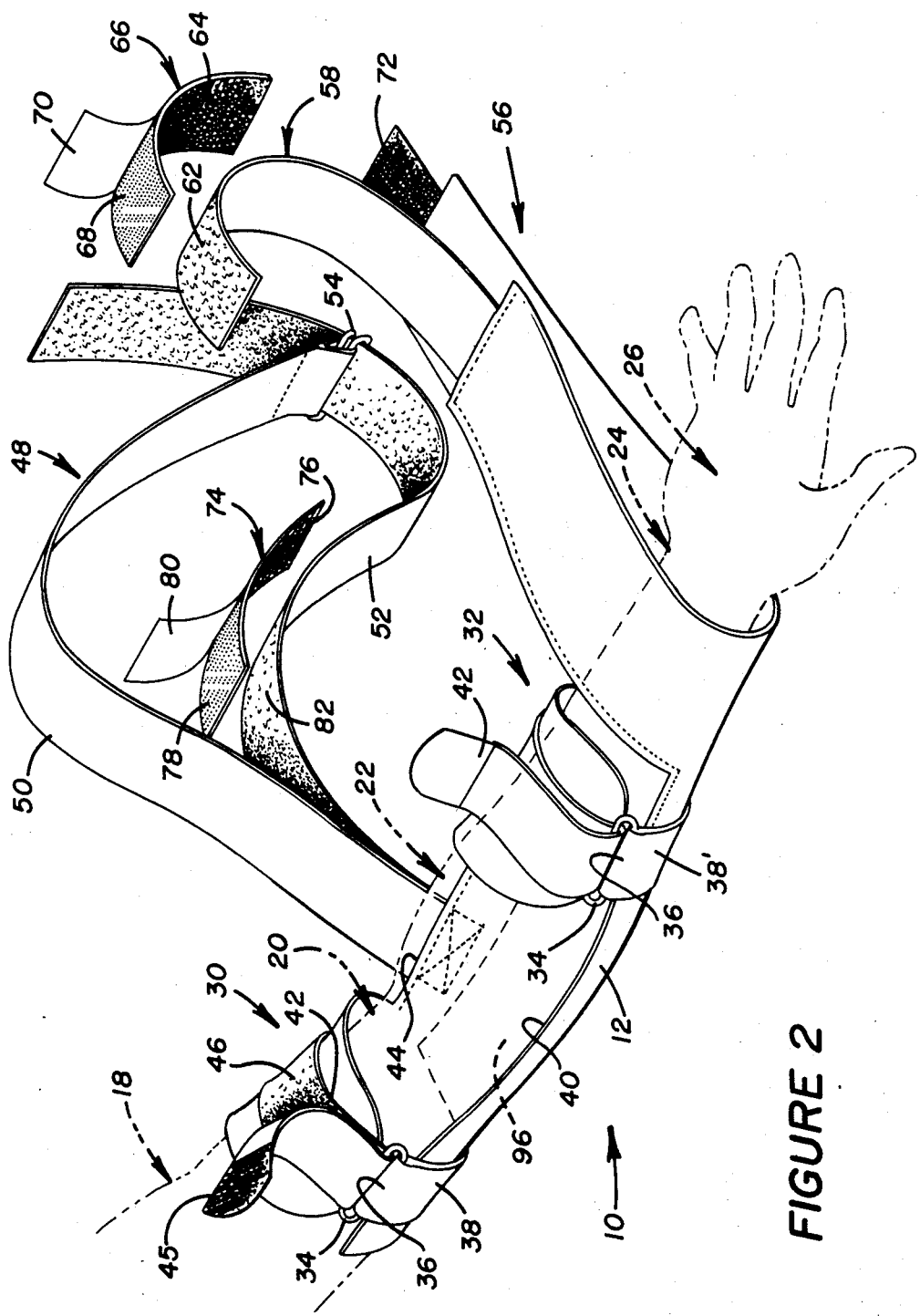
FIG. 2 is an enlarged view of the arm support of the invention, the arm support being engaged with the patient's arm while also illustrating portions of the arm support adapted for engagement with the bed or other adjacent elements to better facilitate positioning of the patient's arm.

Referring now to the drawings in combination, an immobilizing arm support formed in accordance with the present invention is generally indicated at 10 and comprises an elongated flexible sheet 12 suitable for wrapping about the patient's upper and lower arms as illustrated in FIGS. 1 and 2. Preferably, the width of the sheet 12 is selected to leave a portion of the patient's lower or forearm exposed as illustrated in FIGS. 1 and 2 to facilitate the insertion of catheters 13 and the like into the arm.

With the patient 14 being positioned supine on a supporting table 16 or the like, the arm support 10 is intended to immobilize the patient's entire right arm including the upper arm 18, elbow 20, lower or forearm 22, wrist 24 and the hand 26 as discussed in greater detail below. The portion of the forearm 22 left exposed by the flexible sheet 12 is indicated at 28.

Upper and lower strap assemblies 30 and 32 are attached to opposite ends of the sheet 12 and are adapted to be wrapped, along with adjacent portions of the sheet 12, about the upper and lower arms 18 and 22. Each of the strap assemblies 30 and 32 includes a loop or buckle 34 attached to one end 36 of a strap 38 or 38' adjacent one lateral edge 40 of the sheet 12. The other end 42 of each strap extends substantially beyond an opposite lateral edge 44 of the sheet 12. The other end 42 of each strap includes mating fastening means, preferably hook and loop fabric portions, respectively identified at 45 and 46. The hook and loop fabric portions 45 and 46 (best seen in FIG. 3) of the straps 38 and 38' are commercially available under the trademark VELCRO from the Velcro Corporation and permit the straps 38 and 38' to be passed through the buckles 34 and adjustably fastened in snug relation about the patient's arm. The strap 38' is shorter than the strap 38 because of the relatively smaller size of the patient's lower arm 22 relative to the upper arm 18.

A considerably longer immobilizing strap assembly 48 is attached to the sheet 12, preferably in a manner so that the immobilizing strap assembly 48 is adjacent the patient's forearm 22. The strap assembly 48, as illustrated in FIGS. 1 and 2, includes elongated strap portions 50 and 52 with a buckle or other fastener 54 being adapted for adjustably securing the strap portions 50 and 52 together after they are wrapped about the bed 16 as illustrated in FIG. 1. As illustrated in FIG. 1, the immobilizing strap assembly 48 is preferably arranged so that the patient's upper arm 18 is inclined generally downwardly so that a substantial portion of the upper arm and preferably the entire forearm are positioned substantially below the plane of the patient's heart to facilitate angulated imaging as described above.

Thus, it may be seen that through the combination of the flexible sheet 12, the upper and lower strap assemblies 30 and 32, and the immobilizing strap assembly 48, the patient's arm is immobilized in a position closely adjacent to the table 16 and below the plane of the patient's heart to facilitate radiographic imaging of the coronary system and other portions of the patient's chest cavity as well. At the same time, the position of the patient's arm also facilitates positioning and movement of imaging equipment, particularly a C-arm which is commonly adapted for rotation relatively close to the table 16.

In order to prevent relative rotation of the patient's forearm 22 and hand 26, an extension 56 is formed on the sheet 12 and is adapted to be snugly wrapped about the patient's wrist 24 and/or hand 26 to prevent rotation of the forearm 22 and hand 26. An end 58 of the extension 56 is secured in a manner described immediately below to an adjacent element which could be either a portion of the table 16, for example, or the patient's garment 60 as illustrated in FIG. 1.

Referring initially to FIG. 2, a surface portion 62 of the extension 56 and a surface 64 form mating fastening means, preferably a hook and loop fabric of the type also indicated at 45 and 46 and discussed above. The surface 64 is arranged upon a pad 66. An opposite surface 68 of the pad 66 forms adhesive means for attachment of the pad 66 to the patient's garment 60, as illustrated in FIG. 1, following removal of a backing sheet 70.

The extension 56 also includes mating fastening means for securing the extension about the patient's wrist. As illustrated in FIGS. 1 and 2, the mating fastening means for the extension comprises the surface portion 62 and a mating surface portion 72 formed on the opposite end of the extension.

In order to prevent slippage or rotation of the immobilizing strap assembly 48, a pad 74 is provided of similar construction as the pad 66 to provide for non-slip engagement between the immobilizing strap assembly 48 and the table 16. As illustrated in FIG. 2, the pad 74 includes a fabric fastener surface 76 on one side and an adhesive surface 78 on the other side. The adhesive surface 78 is initially covered by backing 80. A surface 82 of the one immobilizing strap 52 includes a mating fabric fastener for engaging the surface 76 of the pad 74.

Thus, upon removal of the backing 80, the adhesive surface 78 permits the pad 74 to be secured to a lower surface of the table as illustrated in phantom in FIG. 1. Thereafter, the surface 82 of the immobilizing strap 52 can be engaged with the surface 76 of the pad to prevent rotation of the immobilizing strap assembly 48.

Referring now to the embodiment or design variation of the arm support as illustrated in FIGS. 3 and 4, the immobilizing strap assembly is indicated at 48' and comprises a single elongated strap 50' having a VELCRO-type fabric fastener surface as indicated at 82'. A first coupler 84 is adjustably connected with the elongated strap 50' adjacent a first end 86. A mating coupler 88 is attached to the other end 90 of the strap 50'. The immobilizing strap assembly 48' of FIGS. 3 and 4 also includes a tab 92 with a fabric-type fastener surface 94 adapted for mating engagement with the surface 82 of the elongated strap 50'. With this arrangement, the immobilizing strap assembly 48' may initially be tightened, for example, about a bed such as that indicated at 16 in FIG. 1 by adjustment of the first coupler 84 on the strap 50' and connection of the mating couplers 84 and 88. With the immobilizing strap assembly 48' thus secured to the bed, as illustrated in FIG. 1, the remaining portion of the arm support 10 may then be attached to the immobilizing strap assembly 48' by engagement of the mating fabric fastener surfaces 82' and 94. The immobilizing strap assembly 48' may also be provided with a non-slip pad 74' substantially similar to the non-slip pad 74 illustrated in FIGS. 1 and 2 and described above.

The two-piece construction for the arm support as described immediately above provides two distinct advantages. Initially, greater access is permitted to the patient's arm even after installation of the arm supprt 10, for example, during cut-down to reach the brachial artery for insertion of the catheter 13 as illustrated in FIG. 1. This may be accomplished by separating the arm support 10 from the immobilizing strap assembly 48' of FIGS. 3 and 4 during cut-down. With the arm support 10 separated from the immobilizing strap assembly 48', the patient's arm may then be moved away from the table 16 (see FIG. 1) in order to perform the cut-down or make an incision in the arm under sterile conditions. With the cut-down complete and the catheter 13 in place, the arm may then be readily moved back adjacent the table 16 with the arm support 10 again being secured to the immobilizing strap assembly 48' with the arm in a position relative to the patient's body and the table 16 as desired for the particular procedure.

In addition, the two-piece construction for the arm support and immobilizing strap assembly 48' facilitates the obtaining of angulated views by conventional radiography equipment. For example, in order to obtain a left anterior oblique (LAO) angulated view, the arm support 10 may similarly be detached from the immobilizing strap assembly 48'. Thereafter, the patient's arm may be moved as necessary to facilitate obtaining of the particular angulated view desired for the procedure. As noted above, sterile conditions may be maintained during obtaining of the angulated view. Thereafter, the patient's arm may again be repositioned by connecting the arm support 10 with the immobilizing strap assembly 48' as discussed above.

The arm support 10 of the present invention also makes provision for the use of a radioluscent rigid arm board 96 if desired during a particular procedure for preventing flexure of the patient's elbow 20. For this purpose, a pocket 98 is formed in the arm support 10 in a position spanning the elbow 20 for receiving the stiffener or rigidifying panel 96 which may thus be seen to serve in the present invention in the nature of an abbreviated arm board. Referring particularly to FIG. 3, the pocket 98 is formed by portions of the straps 38 and 38' which are not sewn to the sheet 12 in order to receive the rigidifying panel 96.

Padding is also formed on the sheet 12 as indicated at 100 and 102 (see FIG. 4) adjacent the upper and lower strap assemblies 30 and 32 in order to protect the patient's upper and lower arms and to better ensure snug engagement of the straps 38 and 38'.

Thus, there has been described a particularly effective and novel unit for supporting and immobilizing a patient's arm to facilitate radiographic imaging of the coronary system and other portions of the body. Various portions of the arm support, particularly the sheet 12, strap assemblies 30 and 32 and rigidifying insert 96 are formed from radioluscent material such as polypropylene in order to prevent interference with radiological imaging techniques. Other variations, in addition to those described herein, will also be obvious from the preceding description. Accordingly, the present invention is defined only by the following appended claims.

What is claimed is:

1. An immobilizing arm support for locating a patient's arm to facilitate angulated radiographic imaging of the patient during angioplasty procedures and the like with the patient being on a supporting table, comprising an elongated sheet of a configuration for being wrapped about the patient's lower arm and upper arm, upper strap means arranged on one end of said sheet for engagement with the patient's upper arm in order to secure said sheet thereto, lower strap means arranged on the other end of said sheet for engagement with the patient's lower arm in order to secure said sheet thereto.

an immobilizing strap secured to a portion of said sheet between said upper strap means and said lower strap means for attachment to the table supporting the patient in order to locate the patient's lower arm generally below the plane of the patient's heart, said portion of said sheet being substantially smaller in width than each of said one end and said other end for leaving a portion of the patients lower arm exposed to permit introduction of a brachial catheter, said immobilizing strap being substantially longer than said upper strap means and said lower strap means to facilitate securement of said immobilizing strap to the supporting table and an extension secured to one end of said elongated sheet adjacent said lower strap means, said extension being of sufficient length to permit its being wrapped about the patient's lower arm adjacent the hand and attached to an adjacent element in order to support and minimize both rotation of the patient's arm and angular movement of the patient's arm relative to said immobilizing strap, said arm support being substantially formed from radioluscent material to facilitate angulated coronary imaging of the patient during angioplasty procedures and the like with minimum interference from the patient's arm and arm support.

2. The immobilizing arm support of claim 1 wherein said immobilizing strap is secured to said portion of said sheet with said portion positionally selected to adapt said immobilizing strap to be locatable adjacent the patient's lower arm and to encircle said table.

3. The arm support of claim 1 further comprising rigidifying means arranged parallel with the patient's arm for minimizing flexure of the patient's elbow.

4. The arm support of claim 1 wherein said elongated sheet comprises pocket means adapted to be arranged parallel with the patient's arm for receiving rigidifying means adapted to minimize flexure of the patient's elbow.

5. The arm support of claim 4 wherein said rigidifying means comprises a radioluscent stiffener element adapted for insertion into said pocket means to extend across the patient's elbow adjacent both the upper and lower arms.

6. The arm support of claim 5 wherein said upper and lower strap means form said pocket means for receiving said stiffener element.

7. The arm support of claim 1 wherein said upper and lower strap means are adjustable.

8. The arm support of claim 7 wherein said upper and lower strap means each comprise adjustable mating fastener means for securing them in engagement about the patient's arm.

9. The arm support of claim 1 wherein said immobilizing strap comprises non-slip means adapted for engagement with the table to prevent rotation of the immobilizing strap about the table and resulting movement of the arm support.

10. The arm support of claim 1 wherein said immobilizing strap comprises non-slip means adapted for engagement with the table to prevent rotation of the immobilizing strap about the table and resulting movement of the arm support.

11. The arm support of claim 10 including a pad means adapted for attachment to the table, said pad means and said non-slip means comprising adjustable mating fastener means.

12. The arm support of claim 1 wherein said extension comprises adjustable mating fastener means for securing it about the patient's lower arm adjacent the hand.

13. The arm support of claim 12 including a pad means adapted for attachment to the adjacent element said pad means and said extension comprising adjustable mating fastener means.

14. The arm support of claim 1 wherein (said extension and) a pad means adapted for attachment to the adjacent element and said extension comprise adjustable mating fastener means.

15. The arm support of claim 14 wherein said pad means comprises an adhesive surface and backing, said backing being removable to expose said adhesive surface for attachment to the adjacent element.

16. The arm support of claim 1 wherein said immobilizing strap is formed as a separate element and further comprising means for selective attachment and detachment between said immobilizing strap and another portion of said arm support.

17. The arm support of claim 16 wherein said attachment and detachment means comprises adjustable mating fastener means.

18. The arm support of claim 17 wherein said adjustable mating fastener means comprise portions respectively of said immobilizing strap and said elongated sheet.

* * * * *